United States Patent [19]
Makita et al.

[11] Patent Number: 5,181,921
[45] Date of Patent: Jan. 26, 1993

[54] DETACHABLE BALLOON WITH TWO SELF-SEALING VALVES

[75] Inventors: Kohzoh Makita; Tohru Machida, both of Tokyo, Japan

[73] Assignee: Kaken Co., Ltd., Tokyo, Japan

[21] Appl. No.: 705,411

[22] Filed: May 24, 1991

[30] Foreign Application Priority Data

May 25, 1990 [JP] Japan ................. 2-55025[U]

[51] Int. Cl.⁵ ............................................ A61M 29/02
[52] U.S. Cl. ........................... 606/195; 604/99; 604/247
[58] Field of Search ............ 604/96, 99, 247; 606/192-195; 623/1, 12

[56] References Cited

U.S. PATENT DOCUMENTS

| Re. 32,348 | 2/1987 | Pevsner. | |
|---|---|---|---|
| 3,502,069 | 3/1970 | Silverman. | |
| 3,542,026 | 11/1970 | Bledsoe | 604/247 |
| 4,085,757 | 4/1978 | Pevsner. | |
| 4,213,461 | 7/1980 | Pevsner. | |
| 4,341,218 | 7/1982 | Ü. | |
| 4,341,224 | 7/1982 | Stevens | 128/675 |
| 4,364,392 | 12/1982 | Strother et al.. | |
| 4,471,779 | 9/1984 | Antoshkiw et al.. | |
| 4,517,979 | 5/1985 | Pecenka. | |
| 4,545,367 | 10/1985 | Tucci | 606/195 X |
| 4,708,718 | 11/1987 | Daniels | 604/53 |
| 4,819,637 | 4/1989 | Dormandy, Jr. et al. | 606/195 |
| 4,836,204 | 6/1989 | Landymore et al.. | |
| 4,932,959 | 6/1990 | Horzewski et al. | 606/194 |
| 4,950,239 | 8/1990 | Gahara et al. | 604/96 |
| 4,976,690 | 12/1990 | Solar et al. | 604/96 |
| 5,015,230 | 5/1991 | Martin et al. | 604/96 |
| 5,085,636 | 2/1992 | Burns | 604/99 |

FOREIGN PATENT DOCUMENTS

| 2637119 | 3/1987 | Fed. Rep. of Germany. | |
|---|---|---|---|
| 3800744 | 5/1989 | Fed. Rep. of Germany | 604/99 |
| 2565828 | 12/1985 | France. | |

Primary Examiner—John D. Yasko
Assistant Examiner—Adam J. Cermak
Attorney, Agent, or Firm—Varndell Legal Group

[57] ABSTRACT

A detachable balloon with two self-sealing valves mounted at the opposite ends thereof. A guide wire and catheter can be inserted through one end of the balloon, and the guide wire extends all the way through the balloon and beyond the balloon out the other end of the balloon, so as to provide easy guidance of the balloon to any desired location in a blood vessel by use of the guide wire. The balloon can also include a material which can be detected by X-rays.

5 Claims, 2 Drawing Sheets

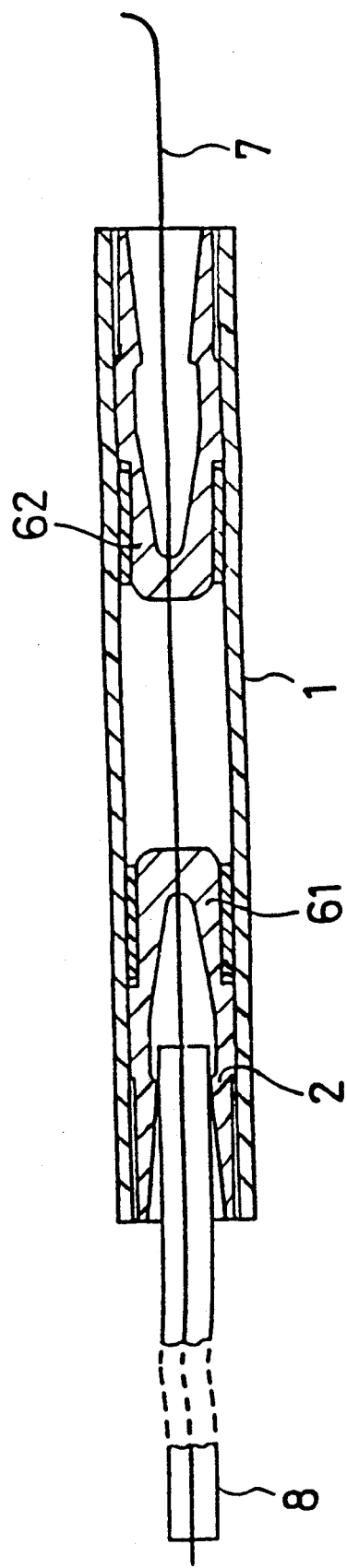

DETACHABLE BALLOON WITH TWO SELF-SEALING VALVES

BACKGROUND OF THE INVENTION

The present invention relates to a detachable balloon catheters with two self-sealing valves and, in particular, to a detachable balloon with two self-sealing valves for blocking or occluding a blood vessel and thereby preventing liquid flow through the blood vessel after the balloon is inflated. The present invention is particularly useful for blocking fluid flow in a region of a blood vessel in front of a diseased part of the blood vessel.

It has become rather routine procedure to use balloons or stoppers to block or occlude blood vessels in certain types of cardiovascular surgery and medical treatments. For example, it is known that a cancer, once developed in a vein, tends to grow gradually by stealing nutrients from the vein. The growth of such a cancer can be inhibited by placing a stopper in the blood vessel so as to inhibit the flow of nutrients to the cancer.

A conventional process of positioning a stopper in a blood vessel includes introducing a stopper into a catheter, forcing a wire tip into the stopper, positioning of the catheter in the region of the blood vessel just before the cancerous part, and withdrawing of the stopper from the catheter by the use of the wire to ensure that the diseased part will be fully sealed or blocked.

Another process involves the steps of attaching a balloon to the tip of a guide wire, the balloon having a check valve mounted on its side for connection with the catheter, pushing the balloon into a blood vessel and positioning the balloon at the area to be sealed, inflating the balloon at the area, and then separating the balloon from the guide wire and the catheter, so that the balloon remains at the area.

One problem with such processes is that they require the use of blood flow for guidance of the balloon to a desired position and, accordingly, the positioning of the stopper is limited by movement of the blood. Therefore, it is very difficult to guide the balloon to the desired position, and such an operation requires a high level of skill.

Another problem with such procedures is that it is very difficult to control the force required to separate the balloon from the wire and catheter. As may be appreciated, if this force is too great, the balloon may be dislodged or repositioned in the blood vessel during detachment of the catheter and guide wire. On the other hand, if the force required to separate the balloon from the catheter and guide wire is too small, the balloon may be prematurely detached during the positioning of the balloon in the blood vessel.

Still another problem with such processes is that if a non-solidifying filler material, such as a saline solution, is used to inflate the balloon, leakage of this material often occurs through the seal of the mouth of the balloon when the catheter and/or wire is separated therefrom.

In this connection, after his elaborate studies for a solution to such problems, the inventor has devised an improved apparatus which can easily position a balloon at an appropriate location in a blood vessel and which includes an improved balloon.

Accordingly, an object of the present invention is to provide the balloon which can be used together with a catheter and wire for permanent occlusion of a blood vessel, where the catheter and guide wire can easily be detached from the balloon after inflation of the balloon and where, prior to the inflation of the balloon, the catheter, guide wire and balloon provide an improved system for guiding the balloon to a desired position within the blood vessel.

Another objective of the present invention is to provide a balloon with two self-sealing valves of improved construction.

SUMMARY OF THE INVENTION

According to one aspect of the present invention, a detachable balloon is provided with two self-sealing valves at the two ends thereof, one end serving as an inlet for receiving a guide wire and a catheter and the other end serving as an outlet which allows the guide wire to pass therethrough. The arrangement of the self-sealing valves of the present invention, together with the guide wire and catheter, provides a superior construction for holding or manipulating the balloon by the guide wire alone, or together with the catheter, so as to prevent premature detachment of the balloon therefrom, to provide easy detachment of the catheter and guide wire from the balloon after inflation of the balloon, and to provide improved positioning of the balloon within a blood vessel. The balloon of the present invention can also include a material which can be sensed by X-rays, namely, a radiopaque material

BRIEF DESCRIPTION OF THE DRAWINGS

FIG. 3 is a cross-sectional view showing the detachable balloon with two self-sealing valves of the present invention together with a guide wire and catheter for inserting the detachable balloon into a blood vessel.

DETAILED DESCRIPTION OF THE PREFERRED EMBODIMENT

The detachable balloon of the present invention has two self-sealing valves mounted on the opposite ends thereof respectively. A guide wire and a catheter can be inserted into the balloon through one of the two self-sealing valves located at one end thereof. The guide wire is extended to such an extent that it can pass through the other of the two self-sealing valves located at the other end of the balloon. The extended guide wire can be freely turned by its tip in any direction. The balloon can be positioned by inserting the guide wire into a desired blood vessel, manually guiding the balloon by manipulation of the guide wire to a desired location in the blood vessel, pulling the tip of the guide wire backward so that it is substantially in the central part of the balloon, inflating the balloon until the sides of the balloon are in contact with the walls of the blood vessel, and then separating the catheter and guide wire from the balloon by slightly pulling the catheter and guide wire therefrom.

Figure 1:
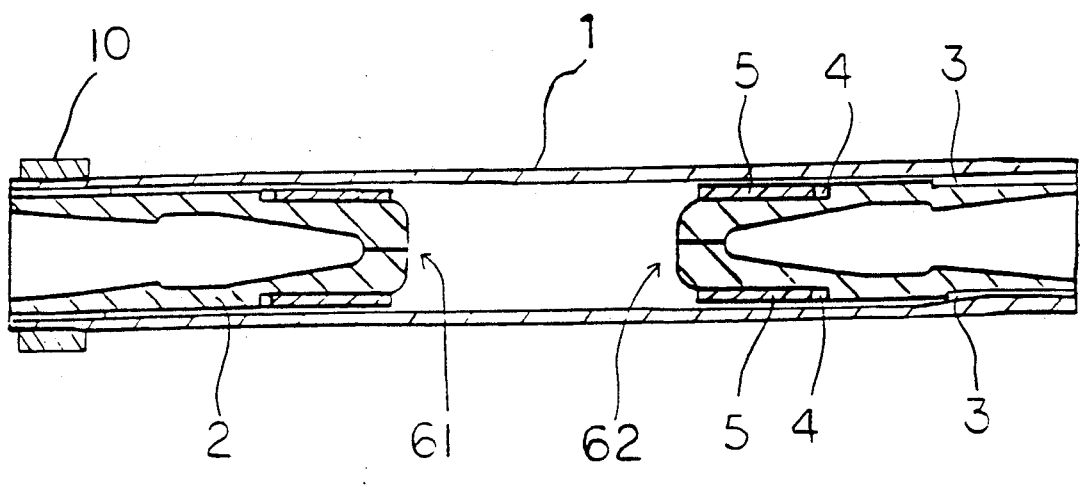
FIG. 1 is a cross-sectional view showing the detachable balloon with two self-sealing valves of the present invention.

The self-sealing valve of the present invention is shown by way of example in FIG. 1. This self-sealing valve is preferably a one-way valve, namely, it allows a liquid to flow therethrough only in one direction and not in the opposite direction. The material of the balloon used in the present invention is not restricted in particular, but it preferably can be rubber-like substances such as silicone rubber, elastomeric rubber, etc. The balloon of the present invention can include some material at least on a portion thereof which can be sensed by X-rays or traced with eyes. Such a material can preferably be metals such as gold, platinum, tungsten, or alloy of these metals. Alternatively, an radiopaque dye can be injected into the interior of the balloon.

The guide wire used in the present invention may be of variety of conventional known materials or structures. Of these guide wires, a preferable use is made of wires composed of coils, springs and cores, or coil springs. The materials for these guide wire can include stainless steel wires, music wires, ultraresilient metallic wires, shape memory alloys, chrome-containing alloys, plastics, etc. The ultraresilient metallic wires and, in particular, the shape memory alloys, are preferably used.

The detachable balloon in accordance with the present invention may be used for sealing diseased parts in blood vessels or veins contracting cancer or the like.

The detachable balloon with two self-sealing valves mounted at the opposite ends thereof enables the guide wire and catheter to be inserted through one self-sealing valve at one end of the balloon. The guide wire extends beyond the length of the balloon and exits the balloon through the self-sealing valve at the other end of the balloon. This arrangement of the guide wire passing through both self-sealing valves of the balloon, alone or in combination with the catheter inserted into one of the self-sealing valves, provides great control over the positioning of the balloon in a blood vessel so that the balloon can be easily guided to any desired direction by using the tip of the guide wire. The interacting forces between the catheter and guide wire can also assist in holding the balloon and/or permitting the balloon to be more easily and precisely manipulated in the blood vessel. This arrangement also permits the guide wire and catheter to be easily separated from the balloon after inflation.

The present invention will be described in further detail with reference to the drawings, but this is only one of the embodiments of the present invention and the present invention is not be limited by this embodiment.

Figure 2:
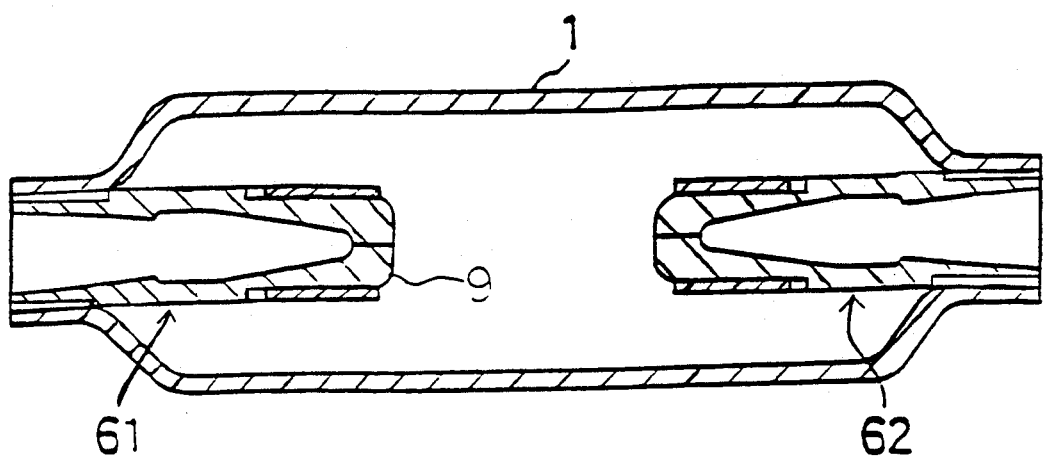
FIG. 2 is a cross-sectional view showing the detachable balloon with two self-sealing valves of FIG. 1 when inflated.

FIG. 1 is a cross sectional view showing the detachable balloon with two self-sealing valves of the present invention, FIG. 2 is a cross sectional view showing the inflated detachable balloon with two self-sealing valves of the present invention as shown by FIG. 1, and FIG. 3 is a cross sectional view showing the detachable balloon with two self-sealing valves of the present invention, including a guide wire and catheter for positioning of the balloon in the blood vessel.

Referring to FIG. 1, balloon 1 includes a self-sealing valves 61, 62 which have a valve base 2; adhesive 3, 4 and a valve cover 5. The balloon and self-sealing valves can be made of a suitable flexible material, such as latex or silicon rubber. The length and diameter of the balloon can be determined by the length and width of the blood vessel into which the balloon is to be inserted. The length and width of the balloon should at least be such, so that when the balloon is expanded, the sides of the balloon can contact the walls of the blood vessel and prevent fluid from flowing therethrough.

As shown, balloon 1 includes self-sealing valves 61, 62 mounted at the opposite ends of the balloon. The valve base 2 of the valves can be fixed to the balloon by an appropriate adhesive 3. The valve cover 5 can also be fixed in position to the valve base 2 by a suitable adhesive 4. If desired the valve cover can be spaced from balloon 1, as shown in FIG. 1. Also, if desired a band of radiopaque material 10 can be provided on the balloon 1, as shown in FIG. 1. When a liquid is injected into the balloon as shown by FIG. 1, the action of the self-sealing valves 61, 62 prevents any backflow of the liquid out of the balloon. Thus, the liquid will be retained within the balloon, so that the balloon will expand, as shown in FIG. 2.

FIG. 3 illustrates a guide wire 7 which extends beyond the length of the balloon and through the both self-sealing valves 61, 62 mounted at the opposite ends of the balloon, so that the tip of the guide wire juts out of one end of the balloon through the self-sealing valve. Catheter 8 can be connected with the valve 61 by insertion into its valve base 2. The outer surface of the catheter and inner surface of base valve base 2 form a fluid tight coupling, so that fluid under pressure can be injected into the interior of balloon 1. The fluid under pressure received from catheter 8 causes the front portion 9 of, for example, the valve 61 to open so that the balloon can be inflated with the fluid.

The guide wire 7 permits manual guiding of the balloon 1 through the blood vessel to the desired location. After the balloon is properly positioned, the guide wire 7 can be fully withdrawn, or partly withdrawn into the interior of the balloon, followed by the injection of a liquid into the balloon. Thereafer, the guide wire can be pulled out of the inflated balloon, and the catheter can be separated from the balloon.

The detachable balloon with two self-sealing valves has improved properties because it can easily be placed in any desired position of the diseased part within the blood vessel by use of a guide wire and/or catheter, while permitting easy detachment of the guide wire and catheter from the balloon after inflation without any dislodging of the inflated balloon and without any leakage of the fluid within the balloon.

While the present invention has been described above primarily with respect to a detachable balloon with two self-sealing valve, it should be apparent that the invention can be employed in a wide variety of vascular catheters which utilize a guide wire. The various modifications and improvements may be made without departing from the scope of the invention.

What is claimed is:

1. A medical instrument comprising a balloon with two self-sealing valves having an inlet for receiving a guide wire and a catheter at one end thereof and an outlet for receiving the guide wire at another end, the two self-sealing valves are arranged at the inlet and outlet respectively and only permit fluid flow into the balloon.

2. The medical instrument of claim 1, including a radiopaque material on an outer surface of the instrument.

3. A medical instrument comprising an inflatable balloon having an elongated shape prior to inflation and first and second self-sealing valves at respective ends thereof, the first and second self-sealing valves permitting fluid flow only into the balloon and including a hollow interior portion surrounded by a valve base adapted to received fluid under pressure so that said valve base separates and permits the fluid to enter and inflate the balloon.

4. The medical instrument of claim 3, further including a catheter and a guidewire and wherein the first self-sealing valve receives the catheter and the guide wire, the guide wire extending through the balloon and through and beyond the second self-sealing valve.

5. The medical instrument of claim 3, further including a catheter and wherein the catheter is received in the valve base of the first self-sealing valve in a fluid-tight relationship.

* * * * *